United States Patent [19]

Eberhard et al.

[11] Patent Number: 4,789,453

[45] Date of Patent: Dec. 6, 1988

[54] ELECTRODES FOR THE COMBINED MEASUREMENT OF OXYGEN AND CARBON DIOXIDE

[75] Inventors: Patrick Eberhard, Allschwil; Wolfgang Mindt, Münchenstein; Jean-Pierre Palma, Pratteln, all of Switzerland

[73] Assignee: Kontron Holding A.G., Zurich, Switzerland

[21] Appl. No.: 147,632

[22] Filed: Jan. 25, 1988

Related U.S. Application Data

[63] Continuation of Ser. No. 55,959, Jun. 1, 1987, abandoned.

[30] Foreign Application Priority Data

Jun. 6, 1986 [CH] Switzerland .............. 2308/86

[51] Int. Cl.$^4$ ............................... G01N 27/30
[52] U.S. Cl. ............................ 204/412; 128/635; 204/403; 204/415
[58] Field of Search ............... 204/412, 403, 415, 1 P, 204/1 K; 128/635

[56] References Cited

U.S. PATENT DOCUMENTS

| 3,227,643 | 1/1966 | Okun et al. .............. 204/415 |
| 3,235,477 | 2/1966 | Keyses et al. ............ 204/415 |
| 3,756,923 | 9/1973 | Dahms et al. ............ 204/1 T |
| 3,785,948 | 1/1974 | Hitchman et al. ........ 204/415 |
| 4,197,853 | 4/1980 | Parker .................... 128/635 |
| 4,303,076 | 12/1981 | Danek et al. .......... 128/635 |

OTHER PUBLICATIONS

W. John Albery et al., J. Electroanalytical Chem., 138, 79–87, (1982).

D. Parker et al., Medical & Biological Eng. & Computing, 16, 599–600, (1978).

Anthony V. Beran et al., Birth Defects: Original Articles Series, vol. XV, No. 4, pp. 421–430, (1979).

*Primary Examiner*—G. L. Kaplan
*Attorney, Agent, or Firm*—Jon S. Saxe; Bernard S. Leon; George W. Johnston

[57] ABSTRACT

A combined sensor for sensing partial $O_2$ pressure and partial $CO_2$ pressure and comprising measuring electrodes, a reference electrode, a diaphragm covering the electrodes and an electrolyte layer between the electrodes and the diaphragm wherein the reference electrode has disposed around it a screening of gold which is at the same potential as the reference electrode and the electrolyte contains a defined concentration of a soluble silver compound or of a silver complex.

5 Claims, 1 Drawing Sheet

ELECTRODES FOR THE COMBINED MEASUREMENT OF OXYGEN AND CARBON DIOXIDE

This application is a continuation of application Ser. No. 55,959, filed June 1, 1987 and now abandoned.

BACKGROUND OF THE INVENTION

1. Field of the Invention

The invention relates to an electrode arrangement for the combined measurement of the partial $O_2$ and $CO_2$ pressures of a medium, the arrangement comprising measuring electrodes and a reference electrode, a diaphragm covering the electrodes and an electrolyte layer between the electrodes and the diaphragm.

2. Description

Electrodes of this kind, also called sensors, are known, inter alia, for the cutaneous measurement of partial $CO_2$ and $O_2$ pressures in the blood. To this end, the tissue is heated at the place of measurement by heating means disposed in the electrode arrangement and thus arterialised.

The measuring electrodes are embodied by a so-called pH glass electrode, for indirect $pCO_2$ measurement, and a platinum microcathode, for $pO_2$ measurement, as are familiar to the expert. The reference electrode is a conventional silver/silver chloride electrode.

Previous experiences with electrodes of this kind have shown that there are two typical and potential sources of error in operation:

1. Irregular deposits of silver, sometimes referred to in the literature as dendrites, form on the measuring electrode which usually takes the form of a platinum microcathode. These deposits gradually increase the area of the cathode and are thus responsible for an unreproducible and uncontrollable drift of the measurement sensitivity of the sensor. Since the silver deposits are to some extent mechanically unstable, they can be separated from the platinum cathode by light pressure on the diaphragm surface, for example, when the sensor is cleaned. The result may be an abrupt alteration in measurement sensitivity which the user often does not notice.

2. Because of the uncontrolled silver deposition, conventional sensors for measuring the partial oxygen pressure need to have the cathode surface cleaned regularly and carefully. This cleaning calls for complicated manual treatment (rubbing) of the cathode surface with a polishing cloth, and the user often finds this treatment tedious. If performed carefully the cleaning completely removes the silver deposit and restores the platinum surface of the cathode to its pure state. When the sensor is used for the first time or is reused after careful cleaning, a fairly long time must elapse before it can make stable measurements. This time is unreproducible and depends upon how carefully the cleaning has been carried out. In many cases the time required for the measuring current to stabilize is longer in proportion as the cleaning was carried out more carefully. Clearly, the user finds this incomprehensible and frustrating and it is a serious disadvantage.

SUMMARY OF THE INVENTION

It has surprisingly been found that stable measurement of the $pO_2$ requires the presence of a thin silver layer on the platinum electrode. New electrodes are devoid of silver layer, whereas the silver layer which forms in operation on electrodes already in use is removed regularly when the surface is given its thorough cleaning (polishing).

The solution of the problem of reducing dendrite formation in the case of electrodes used exclusively for $pO_2$ measurement is useless for combined $pO_2/pCO_2$ sensors. When only $pO_2$ measurement is required, the area of the reference electrode can be reduced so drastically that the quantity of silver ions entering into solution in the reference electrode becomes negligibly small. This step cannot be used for $pCO_2$ measurement since the reference electrode must have a minimum area. The reason for this minimum area is to ensure that the current density produced by the $pO_2$ measurement remains very low so that the $pO_2$ measuring current has a negligible effect on the potential of the reference electrode.

This invention addresses the problem of obviating the uncontrolled dendritic deposition of silver on the $pO_2$ measuring electrode of a combined $pO_2$ and $pCO_2$ sensor and also of producing a defined silver layer on the latter electrode.

According to the invention, therefore, the reference electrode has disposed around it a screening of gold which is at the same potential as the reference electrode and the electrolyte contains a defined concentration of a silver compound or of a silver complex in dissolved form.

BRIEF DESCRIPTION OF THE DRAWINGS

An embodiment of the invention will be described hereinafter with reference to the accompanying drawings wherein.

DETAILED DESCRIPTION OF THE PREFERRED EMBODIMENT

Figure 1:
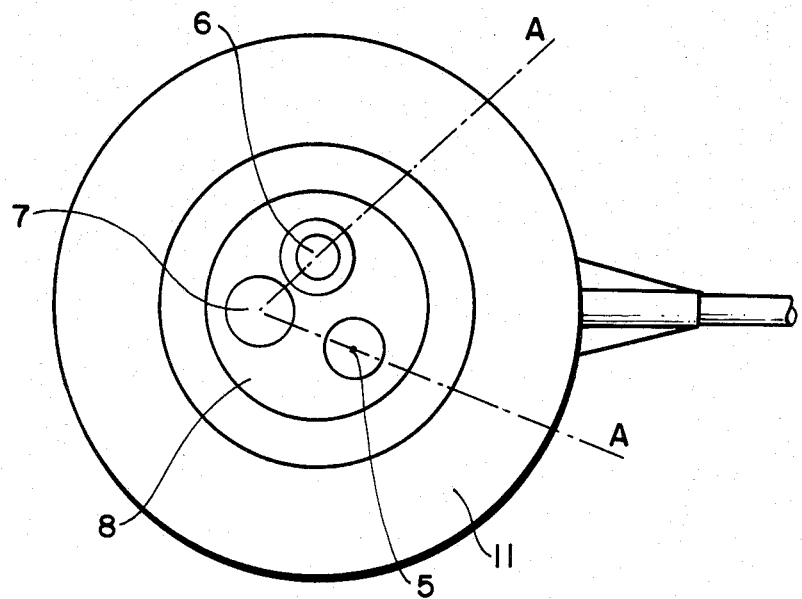
FIG. 1 is a top view of the measuring area of an inventive cutaneous combined $pO_2$ and $pCO_2$ sensor with the diaphragm removed.
Figure 2:
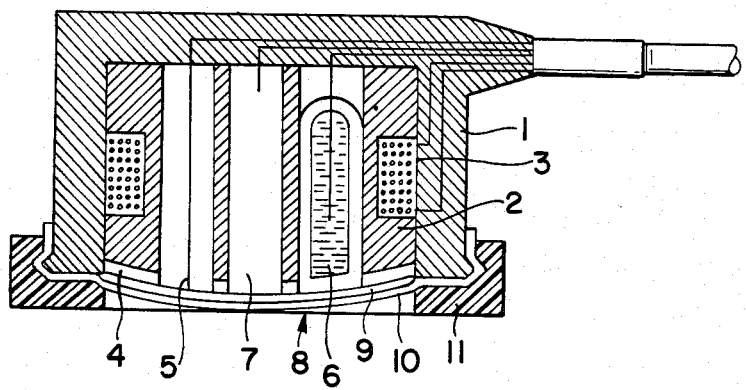
FIG. 2 is a section view taken along line A—A of FIG. 1 through the $pO_2/pCO_2$ electrode.

As can be gathered from FIGS. 1 and 2, the electrode arrangement comprises in conventional manner a casing 1 and, disposed therein, a metal block 2 around which a heating winding 3 is disposed. The block 2 is made of anodized aluminium and has on its exposed surface—the bottom surface in the drawing—a solid gold covering 4. A measuring electrode 5 for $pO_2$, another measuring electrode 6 for $pCO_2$ and a reference electrode 7 are disposed in the block 2. The $pO_2$ electrode 5 is the cathode which in the present case is a microcathode. It is embodied by a platinum wire which is approximately 30 $\mu m$ in diameter and cast in the glass with its end face exposed.

The second measuring electrode 6 for $pCO_2$ is a conventional glass electrode secured with epoxy resin in a corresponding bore.

The reference electrode 7, which is connected as anode for $pO_2$ measurement, is made of silver and is chlorinated on its end face by conventional techniques. In the known cutaneous sensors of this kind the reference electrode is usually arranged as a ring around the measuring electrodes. In the present case, to reduce area the reference electrode is a relatively small circular device and not an annular one. Because of the requirement previously referred to of the current density remaining low, there are of course limits to the extent which the reference electrode can be reduced. The reference electrode has a diameter of at least about one-tenth and at most about one-third of the diameter of the entire active sensor area of measuring sensor 8.

The measuring electrodes 5, 6 and the reference electrode 7 are so disposed in the metal block 2 as to form a common convex end face or measuring surface 8. The same is covered by an electrolyte layer 9 which is in turn covered by a semi-permeable diaphragm 10 retained and clamped by a clamping ring 11.

The diaphragm 10 is made of polytetrafluoroethylene (Teflon) or some other plastics known and conventional for this particular application.

The reduction in size of the reference electrode reduces the amount of silver entering into solution and thus reduces dendrite formation on the cathode. Of course, the limits on the extent to which the reference electrode can be reduced are not an adequate barrier to dendrite formation; however, the gold covering 4 which extends completely around the reference electrode intercepts any further silver ions which would otherwise reach the microcathode. The intercepting effect of the gold therefore reduces the tendency to dendrite formation to negligibly small proportions.

Since less silver is dissolved or reaches the reference electrode, it takes longer for the bare microcathode to "silver up" and, therefore, for measurement stability to be reached. To ensure a controlled separation of silver on the cathode, silver is added to the electrolyte in an appropriate soluble compound or in a soluble complex. This step even makes it possible, as a result of controlled silver separation, to reduce the time needed for measurement stability to be reached.

As soluble silver compound there can be considered the following compounds: AgCl, AgCN, AgNO$_3$. As complexing agent for silver there can be considered e.g. ethylene diamide tetraacetic acid (EDTA) and diethylene triamine pentaacetic acid (DTPA). The concentration of the silver added to the electrolyte is typically of the order of magnitude of from about 10 to about $100 \times 10^{-6}$ mol/l.

While the invention has been described in conjunction with certain embodiments, it is understood that various modifications and changes may be made without departing from the spirit and scope of the invention.

We claim:

1. An electrode arrangement for the combined measurement of the partial $O_2$ and $CO_2$ pressures of a medium, the arrangement comprising measuring electrodes, one of which applies for $PO_2$ and the other applies for $PCO_2$, a reference electrode, a diaphragm covering the electrodes and an electrolyte layer between the electrodes and the diaphragm, the reference electrode has disposed thereon a layer of gold which is at the same potential as the reference electrode and the electrolyte contains a predetermined concentration of a soluble silver compound or of a silver complex.

2. The electrode arrangement of claim 1, wherein the reference electrode has a circular surface with a diameter of at least about one-tenth and at most about one-third of the diameter of the total measuring area of the electrode.

3. The electrode arrangement of claim 1, wherein the soluble silver compound is selected from the group consisting of AgCl, AgCN, and AgNO$_3$.

4. The electrode arrangement of claim 1, wherein the silver complex is formed by complexing silver with a complexing agent selected from the group consisting of EDTA and DTPA.

5. The electrode arrangement of claim 1, wherein the electrolyte contains about 10 to about $100 \times 10^{-6}$ mol/l of silver.

* * * * *